United States Patent
Hiratsuka et al.

(10) Patent No.: US 10,932,856 B2
(45) Date of Patent: Mar. 2, 2021

(54) SURGICAL SYSTEM CONTROL METHOD AND SURGICAL SYSTEM

(71) Applicant: KAWASAKI JUKOGYO KABUSHIKI KAISHA, Kobe (JP)

(72) Inventors: Mitsuichi Hiratsuka, Kobe (JP); Tetsuya Nakanishi, Kobe (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 367 days.

(21) Appl. No.: 16/093,757

(22) PCT Filed: Apr. 12, 2017

(86) PCT No.: PCT/JP2017/014999
§ 371 (c)(1),
(2) Date: Oct. 15, 2018

(87) PCT Pub. No.: WO2017/179624
PCT Pub. Date: Oct. 19, 2017

(65) Prior Publication Data
US 2019/0117310 A1 Apr. 25, 2019

(30) Foreign Application Priority Data
Apr. 15, 2016 (JP) .............. JP2016-081692

(51) Int. Cl.
B25J 9/16 (2006.01)
A61B 34/10 (2016.01)
(Continued)

(52) U.S. Cl.
CPC .............. *A61B 34/10* (2016.02); *A61B 34/20* (2016.02); *A61B 34/35* (2016.02); *A61B 34/37* (2016.02);
(Continued)

(58) Field of Classification Search
USPC .................................. 700/245–264
See application file for complete search history.

(56) References Cited

U.S. PATENT DOCUMENTS 6,799,065 B1* 9/2004 Niemeyer .......... A61B 1/00149
600/407
7,607,440 B2* 10/2009 Coste-Maniere ...... A61B 34/70
128/898
(Continued)

FOREIGN PATENT DOCUMENTS

JP 2000-300579 A 10/2000
WO 2015/120008 A1 8/2015

Primary Examiner — Jonathan L Sample
(74) Attorney, Agent, or Firm — Oliff PLC

(57) ABSTRACT

Simulated are postures each formed by a manipulator arm and a surgical instrument when a tip end portion of the surgical instrument is located at a three-dimensional position of each lattice point in a lattice model set so as to correspond to the manipulator arm, the surgical instrument being held by the manipulator arm. Extracted is such a combination of the lattice points in the lattice models that the postures interfere with each other. Data of the combination which causes the interference is stored in a storage portion. It is determined whether or not an operating command transferred to a control portion corresponds to the combination which causes the interference. When it is determined that the operating command corresponds to the combination which causes the interference, the control portion executes interference preventing processing.

8 Claims, 7 Drawing Sheets

(51) Int. Cl.
*A61B 34/20* (2016.01)
*A61B 34/35* (2016.01)
*A61B 34/37* (2016.01)
*A61B 34/00* (2016.01)
*A61B 34/30* (2016.01)
*A61B 90/00* (2016.01)
*G06T 1/00* (2006.01)
*G06T 7/00* (2017.01)

(52) U.S. Cl.
CPC .......... *A61B 34/70* (2016.02); *B25J 9/1676* (2013.01); *B25J 9/1689* (2013.01); *A61B 34/25* (2016.02); *A61B 90/361* (2016.02); *A61B 90/37* (2016.02); *A61B 2034/107* (2016.02); *A61B 2034/301* (2016.02); *G05B 2219/40418* (2013.01); *G06T 1/0014* (2013.01); *G06T 7/0012* (2013.01)

(56) References Cited

U.S. PATENT DOCUMENTS

| | | | |
|---|---|---|---|
| 9,259,280 B2 * | 2/2016 | Au | A61B 34/37 |
| 2007/0293734 A1 * | 12/2007 | Coste-Maniere | A61B 34/35 |
| | | | 600/300 |
| 2010/0036393 A1 * | 2/2010 | Unsworth | A61B 90/361 |
| | | | 606/130 |
| 2010/0274087 A1 * | 10/2010 | Diolaiti | A61B 90/37 |
| | | | 600/118 |
| 2011/0107270 A1 * | 5/2011 | Wang | G16H 20/40 |
| | | | 715/850 |
| 2012/0059391 A1 * | 3/2012 | Diolaiti | B25J 9/1689 |
| | | | 606/130 |
| 2014/0163736 A1 * | 6/2014 | Azizian | A61B 6/4441 |
| | | | 700/259 |

* cited by examiner

SURGICAL SYSTEM CONTROL METHOD AND SURGICAL SYSTEM

TECHNICAL FIELD

The present invention relates to a surgical system control method and a surgical system.

BACKGROUND ART

A master-slave system is known, which includes a plurality of manipulator arms and performs surgery by moving the plurality of manipulator arms based on manipulations of an operator (see PTLs 1 and 2, for example). In such system, the plurality of manipulator arms are arranged very close to one another so as to be able to perform a fine medical treatment with respect to one treated part while cooperating with one another.

According to industrial robots, the movements of the robots are determined in advance. Therefore, even when there exist a plurality of arms, the order of operations is set in advance such that the arms do not interfere with one another, and with this, the interference of the arms during the operations can be prevented. However, the plurality of manipulator arms of the surgical system need to operate based on an operating command of the operator in real time. On this account, even if simulation is performed in advance like the simulation performed for the industrial robots, the interference of the manipulator arms located close to each other cannot be prevented.

PTL 1 proposes that the interference of a plurality of manipulator arms is prevented by optimizing opening positions of a patient by simulation, the opening positions being provided for respective manipulator arms for allowing the manipulator arms to access a treated region in a body of the patient.

PTL 2 proposes that: coordinates occupied by respective manipulator arms when the manipulator arms move are calculated; and whether or not the manipulator arms interfere with one another is calculated based on the coordinates.

CITATION LIST

Patent Literature

PTL 1: U.S. Patent Application Publication No. 2007/0293734
PTL 2: Japanese Laid-Open Patent Application Publication No. 2000-300579

SUMMARY OF INVENTION

Technical Problem

However, according to the above aspects, there are the following problems. To be specific, according to the aspect of PTL 1, when the opening positions cannot be set freely, such as when a medical treatment is performed by inserting the surgical instruments between the ribs, optimizing the opening positions to prevent the interference of the manipulator arms may not be possible. Further, even if the opening positions are optimized to prevent the interference, the opening positions may not be located at positions which are easy for an operator, who actually conducts the medical treatment, to conduct the medical treatment.

According to the aspect of PTL 2, after the reception of a movement command from the operator, whether or not the manipulator arms holding the respective surgical instruments interfere with one another is calculated from (i) a current position and movement target position of the surgical instrument moved by the movement command and (ii) current positions of the other surgical instruments. If it is determined that the manipulator arms interfere with each other, warning is executed, for example. As above, according to the aspect of PTL 2, whether or not the interference of the manipulator arms holding the surgical instruments occurs needs to be calculated before the manipulator arms are moved or while the manipulator arms are moving. Therefore, to execute waring in advance to the operator to prevent the manipulator arms or the surgical instruments from actually contacting each other when it is determined that the interference occurs, movement speeds of the manipulator arms need to be limited to certain speeds or less. Therefore, according to this aspect, the surgical instruments may not follow the operating command input by the operator, or a time difference may be generated between the input of the operator and the actual movement of the surgical instrument. Thus, the accuracy of the medical treatment cannot be improved.

The present invention was made to solve the above problems, and an object of the present invention is to provide a surgical system control method and a surgical system, by each of which a plurality of manipulator arms are prevented from interfering with one another without influencing a medical treatment.

Solution to Problem

An aspect of the present invention is a method of controlling a surgical system, the surgical system including: a plurality of manipulator arms each including a tool holding portion at a tip end portion of the manipulator arm, the tool holding portion being configured to hold a long shaft-shaped surgical instrument, the tip end portion of the manipulator arm being configured to three-dimensionally move relative to a base end portion of the manipulator arm; a manipulating apparatus to which an operating command is input, the operating command being for moving the plurality of manipulator arms; a control portion configured to control the movements of the plurality of manipulator arms based on the operating command; and a storage portion from which the control portion reads out data, the method including: setting as a constraint point a predetermined position between the tip end portion of each manipulator arm and a tip end portion of the surgical instrument held by the manipulator arm; setting a predetermined lattice model created by arranging a plurality of lattice points on a surface of a predetermined stereoscopic shape defining a three-dimensional movement range of the tip end portion of the surgical instrument when the manipulator arm is three-dimensionally moved with a three-dimensional position of the constraint point fixed; simulating a first posture formed by a first manipulator arm and a first surgical instrument when a tip end portion of the first surgical instrument is located at the three-dimensional position of each lattice point in a first lattice model set so as to correspond to the first manipulator arm, the first surgical instrument being held by the first manipulator arm; simulating a second posture formed by a second manipulator arm and a second surgical instrument when a tip end portion of the second surgical instrument is located at the three-dimensional position of each lattice point in a second lattice model set so as to correspond to the second manipulator arm, the second manipulator arm being located adjacent to the first manipulator arm, the second surgical instrument being held by the second manipulator arm; extracting such a combination of the lattice point in the first lattice model and the lattice point in the second lattice model that the first posture and the second posture interfere with each other; storing, in the storage portion, data of the combination which causes the interference; determining whether or not the operating command transferred to the control portion corresponds to the combination which causes the interference; and executing interference preventing processing by the control portion when it is determined that the operating command corresponds to the combination which causes the interference.

According to the above control method, a position corresponding to an opening position at which a surgical instrument is inserted into a body of a patient is set as the constraint point. Further, set is the predetermined lattice model created by arranging the plurality of lattice points on the surface of the predetermined stereoscopic shape defining the three-dimensional movement range of the tip end portion of the surgical instrument when the manipulator arm is three-dimensionally moved with the three-dimensional position of the constraint point fixed. The posture formed by the manipulator arm and the surgical instrument when the tip end portion of the surgical instrument is located at each lattice point constituting the lattice model set for the manipulator arm is simulated. It is determined whether or not the first posture formed by the first manipulator arm and the first surgical instrument and the second posture formed by the adjacent second manipulator arm and the second surgical instrument interfere with each other. Then, the combinations of the lattice points which cause the interference are stored in the storage portion of the surgical system before the medical treatment. When it is determined during the medical treatment that the combination of the postures of the plurality of manipulator arms based on the operating command input by the operator corresponds to the combination of the lattice points which cause the interference, the interference preventing processing is executed to prevent the interference from actually occurring. As above, the combinations which cause the interference of the first and second postures are extracted in advance by round-robin determination for the plurality of lattice points defining the movement ranges set for the respective manipulator arms. With this, processing of avoiding the interference can be performed without performing complex calculations while moving the manipulator arms during the medical treatment. Therefore, the plurality of manipulator arms can be prevented from interfering with one another without influencing the medical treatment.

The stereoscopic shape may be a sphere, and position coordinates of each lattice point in the first and second lattice models may be determined based on (i) position coordinates of a center point of a section of the sphere, the section being perpendicular to a straight line coupling the corresponding constraint point and a center of the sphere, (ii) a radius of the section, and (iii) an angle from a predetermined reference position on each lattice model. With this, the position coordinates of the lattice points can be easily determined, and the positions of the combinations which cause the interference can be easily recognized.

The surgical system may include a predetermined informing portion, and the interference preventing processing may include an output of a warning from the informing portion. With this, the input of the operating command which causes the interference can be quickly informed to the operator.

As the interference preventing processing, the control portion may prevent at least one of the first manipulator arm and the second manipulator arm from moving to a position of the combination which causes the interference. With this, even when the operating command which causes the interference is input, the interference can be prevented from actually occurring.

Each of the plurality of manipulator arms may be configured as a seven-axis articulated arm including a redundant axis, the arm being configured to change a posture of the arm without changing a position of the tip end portion of the arm, and when the combination which causes the interference is extracted, it may be redetermined whether or not the interference occurs by changing at least one of the first posture and the second posture without changing the position of the tip end portion of each manipulator arm. With this, the number of combinations which cause the interference can be reduced as much as possible.

Each of a center position of the first lattice model and a center position of the second lattice model may be located at the same position as a center position of the corresponding stereoscopic shape, and each of the first lattice model and the second lattice model may include lattice points arranged on a surface of a shape similar to but smaller than the corresponding stereoscopic shape. With this, the posture formed by the manipulator arm and the surgical instrument when the tip end portion of the surgical instrument is located inside the movement range can also be considered. Thus, the determination of the interference can be performed more accurately.

A surgical system control method according to another aspect of the present invention is a method of controlling a surgical system, the surgical system including: a plurality of manipulator arms each including a tool holding portion configured to hold a surgical instrument; a control portion configured to control movements of the plurality of manipulator arms based on an operating command; and a storage portion connected to the control portion, the method including: setting a first reference point as a position of a first surgical instrument held by a first manipulator arm; setting a first point group model created by arranging a plurality of points in a movement range of the first reference point; simulating a first posture formed by the first manipulator arm and the first surgical instrument when the first reference point is located at a position of each point in the first point group model; setting a second reference point as a position of a second surgical instrument held by a second manipulator arm; setting a second point group model created by arranging a plurality of points in a movement range of the second reference point; simulating a second posture formed by the second manipulator arm and the second surgical instrument when the second reference point is located at a position of each point in the second point group model; storing, in the storage portion, data of such a combination of the point in the first point group model and the point in the second point group model that the first manipulator arm and the first surgical instrument in the first posture and the second manipulator arm and the second surgical instrument in the second posture interfere with each other; determining whether or not positions of the first and second reference points corresponding to the operating command transferred to the control portion correspond to the stored data of the combination; and executing interference preventing processing by the control portion when it is determined that the positions correspond to the stored data.

According to the above control method, the positions of the surgical instruments are set as the reference points. Further, the positions of the plurality of manipulator arms and the surgical instruments are simulated by using the point group models, on each of which the plurality of points are arranged, as the movement ranges of the reference points. With this, it is determined whether or not the first posture formed by the first manipulator arm and the first surgical instrument and the second posture formed by the adjacent second manipulator arm and the second surgical instrument interfere with each other. Then, the combinations of the points which cause the interference are stored in the storage portion of the surgical system before the medical treatment. When it is determined during the medical treatment that the combination of the postures of the plurality of manipulator arms based on the operating command input by the operator corresponds to the combination of the points which cause the interference, the interference preventing processing is executed to prevent the interference from actually occurring. As above, the combinations which cause the interference of the first and second postures are determined by using the point group models defining the movement ranges set for the respective manipulator arms. With this, the processing of avoiding the interference can be performed without performing complex calculations while moving the manipulator arms during the medical treatment. Therefore, the plurality of manipulator arms can be prevented from interfering with one another without influencing the medical treatment.

A surgical system according to yet another aspect of the present invention is a surgical system including: a plurality of manipulator arms each including a tool holding portion at a tip end portion of the manipulator arm, the tool holding portion being configured to hold a long shaft-shaped surgical instrument, the tip end portion of the manipulator arm being configured to three-dimensionally move relative to a base end portion of the manipulator arm; a manipulating apparatus to which an operating command is input, the operating command being for moving the plurality of manipulator arms; a control portion configured to control the movements of the plurality of manipulator arms based on the operating command; and a storage portion from which the control portion reads out data, wherein: a first lattice model is set so as to correspond to a first manipulator arm and is created by arranging a plurality of lattice points on a surface of a predetermined stereoscopic shape defining a three-dimensional movement range of a tip end portion of a first surgical instrument held by the first manipulator arm; a second lattice model is set so as to correspond to a second manipulator arm located adjacent to the first manipulator arm and is created by arranging a plurality of lattice points on a surface of a stereoscopic shape defining a three-dimensional movement range of a tip end portion of a second surgical instrument held by the second manipulator arm; the storage portion stores data of such a combination of the lattice point in the first lattice model and the lattice point in the second lattice model that a first posture formed by the first manipulator arm and the first surgical instrument when the tip end portion of the first surgical instrument is located at a three-dimensional position of each lattice point in the first lattice model and a second posture formed by the second manipulator arm and the second surgical instrument when the tip end portion of the second surgical instrument is located at a three-dimensional position of each lattice point in the second lattice model interfere with each other; the control portion determines whether or not the received operating command corresponds to the combination which causes the interference; and when it is determined that the operating command corresponds to the combination which causes the interference, the control portion executes interference preventing processing.

According to the above configuration, such a combination of the lattice point in the first lattice model and the lattice point in the second lattice model that the first posture and the second posture interfere with each other is stored in the storage portion in advance, the first posture being formed by the first manipulator arm and the first surgical instrument when the tip end portion of the first surgical instrument held by the first manipulator arm is located at the three-dimensional position of each lattice point in the first lattice model set so as to correspond to the first manipulator arm, the second posture being formed by the second manipulator arm and the second surgical instrument when the tip end portion of the second surgical instrument held by the second manipulator arm is located at the three-dimensional position of each lattice point in the second lattice model set so as to correspond to the second manipulator arm located adjacent to the first manipulator arm. When it is determined during the medical treatment that the combination of the postures of the plurality of manipulator arms based on the operating command input by the operator corresponds to the combination of the lattice points which cause the interference, the interference preventing processing is executed to prevent the interference from actually occurring. As above, the combinations which cause the interference of the first and second postures are extracted in advance by the round-robin determination for the plurality of lattice points defining the movement ranges set for the respective manipulator arms. With this, the processing of avoiding the interference can be performed without performing complex calculations while moving the manipulator arms during the medical treatment. Therefore, the plurality of manipulator arms can be prevented from interfering with one another without influencing the medical treatment.

The above object, other objects, features, and advantages of the present invention will be made clear by the following detailed explanation of preferred embodiments with reference to the attached drawings.

Advantageous Effects of Invention

The present invention has an effect of being able to prevent a plurality of manipulator arms from interfering with one another without influencing a medical treatment.

DESCRIPTION OF EMBODIMENTS

Hereinafter, an embodiment of the present invention will be explained with reference to the drawings. It should be noted that the present invention is not limited to the present embodiment. In the following explanations and the drawings, the same reference signs are used for the same or corresponding components, and a repetition of the same explanation is avoided.

Figure 1:
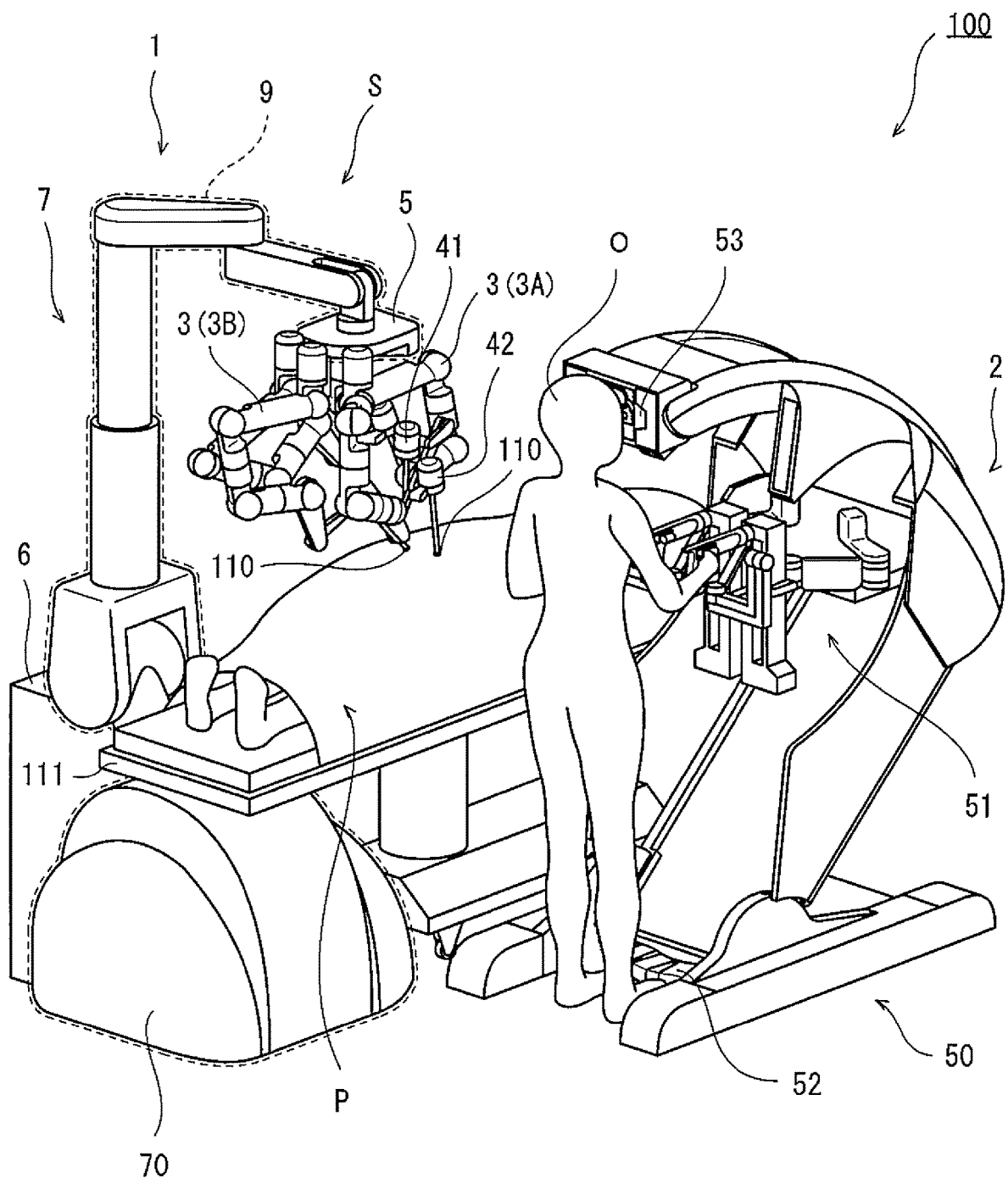
FIG. 1 is a schematic diagram showing an entire configuration of a surgical system according to one embodiment of the present invention.

FIG. 1 is a schematic diagram showing an entire configuration of a surgical system 100 according to one embodiment of the present invention. As shown in FIG. 1, the surgical system 100 is a system by which an operator O, such as a doctor, performs an endoscope surgery for a patient P by using a patient-side system 1, like a robot assisted surgery, a robot remote surgery, etc.

The surgical system 100 includes the patient-side system 1 and a manipulating apparatus 2 configured to manipulate the patient-side system 1. The manipulating apparatus 2 is arranged away from the patient-side system 1, and the patient-side system 1 is remotely controlled by the manipulating apparatus 2. The operator O inputs to the manipulating apparatus 2 an operation to be performed by the patient-side system 1, and the manipulating apparatus 2 transmits the operating command to the patient-side system 1. Then, the patient-side system 1 receives the operating command transmitted from the manipulating apparatus 2 and operates an endoscope assembly 41, instruments (surgical instruments) 42, and the like included in the patient-side system 1 based on the operating command.

The manipulating apparatus 2 constitutes an interface between the surgical system 100 and the operator O and is an apparatus configured to manipulate the patient-side system 1. The manipulating apparatus 2 is provided beside an operating table 111 in an operating room, away from the operating table 111, or outside the operating room. The manipulating apparatus 2 includes: a manipulation input portion 50 to which the operator O inputs the operating command; and a monitor 53 configured to display an image taken by the endoscope assembly 41. The manipulation input portion 50 includes an operation manipulator arm 51, an operation pedal 52, and the like. While visually confirming an affected part on the monitor 53, the operator O manipulates the manipulation input portion 50 to input the operating command to the manipulating apparatus 2. The operating command input to the manipulating apparatus 2 is transferred to a below-described controller 6 of the patient-side system 1 through a wire or wirelessly.

The patient-side system 1 constitutes an interface between the surgical system 100 and the patient P. The patient-side system 1 is arranged beside the operating table 111 on which the patient P lies in the operating room. An inside of the operating room is a sterile field where sterilization is performed.

The patient-side system 1 includes: a positioner 7; a platform 5 attached to a tip end portion of the positioner 7; and a plurality of patient-side manipulator arms (hereinafter simply referred to as "arms 3") detachably attached to the platform 5. The positioner 7 is configured as a horizontal articulated robot and can three-dimensionally move the position of the platform 5 relative to a base 70 placed at a predetermined position in the operating room. The positioner 7 and the platform 5 are covered with a sterile drape 9, and with this, the positioner 7 and the platform 5 are shielded from the sterile field in the operating room.

The endoscope assembly 41 is held by a tip end portion of an arm 3A that is one of the plurality of arms 3. The instruments 42 are detachably held by respective tip end portions of arms 3B that are the remaining ones of the plurality of arms 3. Hereinafter, the arm 3 to which the endoscope assembly 41 is attached may be referred to as a "camera arm 3A", and the arm 3 to which the instrument 42 is attached may be referred to as an "instrument arm 3B." The patient-side system 1 of the present embodiment includes four arms 3 that are one camera arm 3A and three instrument arms 3B.

The patient-side system 1 is controlled by the controller 6. The controller 6 is constituted by a computer, such as a microcontroller.

In the patient-side system 1, the platform 5 serves as a "hub" that is a base of the plurality of arms 3. In the present embodiment, the positioner 7 and the platform 5 constitute a manipulator arm support S movably supporting the plurality of arms 3. It should be noted that the manipulator arm support S is only required to include at least the platform 5. The manipulator arm support S may be constituted by the platform 5 supported by a linear motion rail, a lifting device, a bracket attached to a ceiling or a wall, or the like instead of the positioner 7.

In the patient-side system 1, a series of components are connected to one another from the positioner 7 to the endoscope assembly 41 or to the instrument 42. In the present specification, regarding each of the series of components, an end portion located close to the positioner 7 (more specifically, a portion of the positioner 7 which portion contacts a floor of the operating room) is referred to as a "base end portion," and an end portion opposite to the base end portion is referred to as a "tip end portion."

Figure 2:
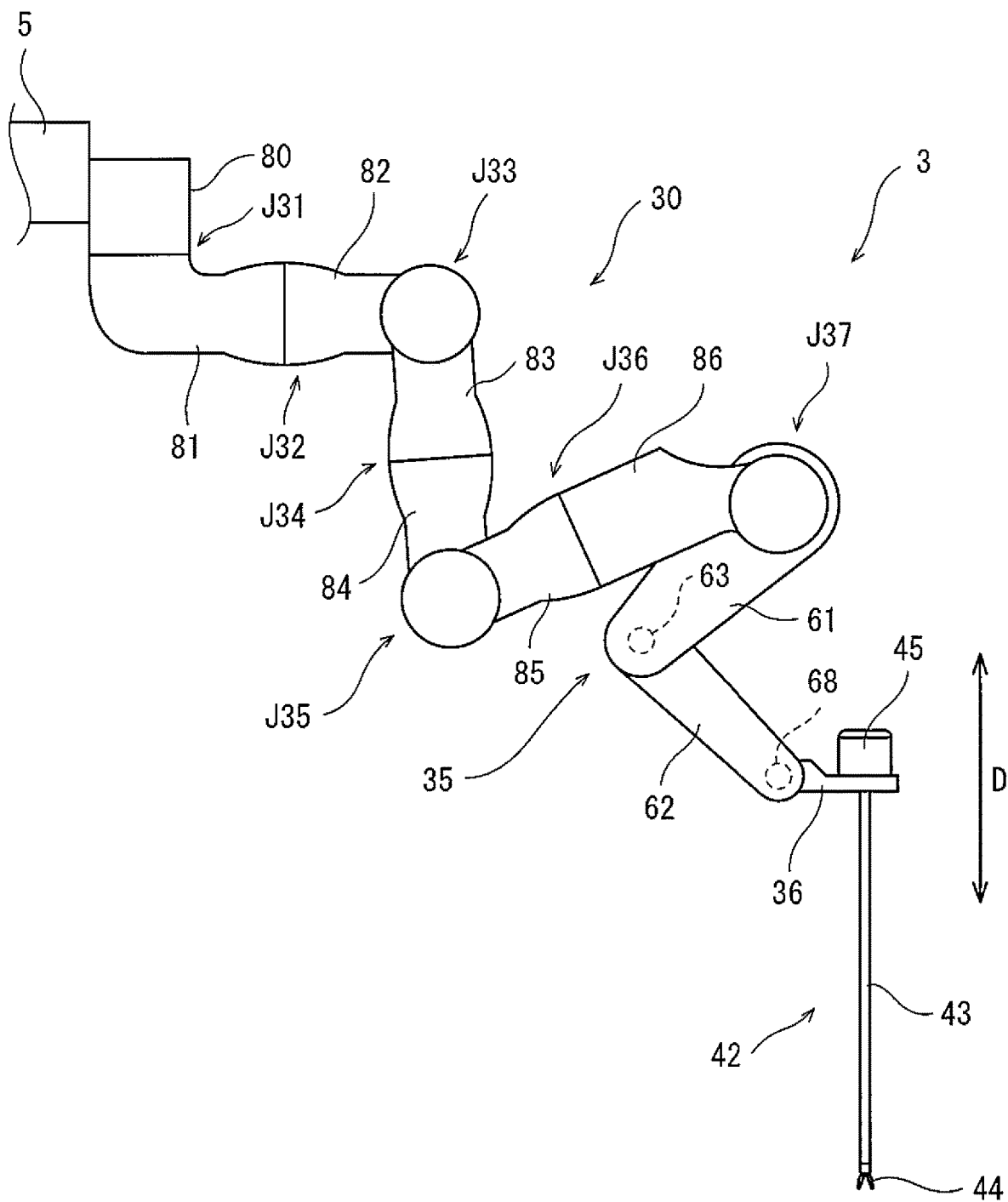
FIG. 2 is a schematic diagram showing an entire configuration of a manipulator arm of a patient-side system of the surgical system of FIG. 1.

The instrument 42 includes: a drive unit 45 provided at the base end portion of the instrument 42; an end effector (treatment tool) 44 provided at the tip end portion of the instrument 42; and a long and thin shaft 43 connecting the drive unit 45 and the end effector 44 (see FIG. 2). A long axis direction D is defined for the instrument 42. The drive unit 45, the shaft 43, and the end effector 44 are arranged along the long axis direction D. The end effector 44 of the instrument 42 is selected from the group consisting of: tools including operating joints (such as forceps, scissors, a grasper, a needle holder, a microdissector, a staple applier, a tucker, a suction cleaning tool, a snare wire, and a clip applier); and tools not including joints (such as a cutting blade, a cautery probe, a cleaning tool, a catheter, and a suction orifice). A "long shaft-shaped surgical instrument" recited in the present specification and claims denotes the endoscope assembly 41 or the instrument 42.

In the medical treatment using the patient-side system 1 configured as above, first, the controller 6 which has received the operating command from the manipulating apparatus 2 operates the positioner 7 to position the platform 5 such that a predetermined positional relation between the platform 5 and the operating table 111 or between the platform 5 and the patient P is realized. Next, the controller 6 operates the arms 3 to position the endoscope assembly 41 and the instruments 42 such that a predetermined initial positional relation among the endoscope assembly 41, the instruments 42, and sleeves (cannula sleeves) 110 placed on a body surface of the patient P is realized. It should be noted that the positioning operation of the positioner 7 and the positioning operation of the arms 3 may be performed at the same time. Then, with the positioner 7 generally in a stationary state, the controller 6 operates the arms 3 in accordance with the operating command from the manipulating apparatus 2. Thus, the controller 6 operates the instruments 42 to perform the medical treatment while suitably displacing the endoscope assembly 41 and the instruments 42 and changing postures of the endoscope assembly 41 and the instruments 42.

The configuration of the arm 3 will be explained in detail. FIG. 2 is a schematic diagram showing an entire configuration of the manipulator arm of the patient-side system of the surgical system of FIG. 1. FIG. 2 shows the schematic configuration of one of the plurality of arms 3 included in the patient-side system 1. As shown in FIG. 2, the arm 3 includes: an arm main body 30; and a translational arm 35 coupled to the tip end portion of the arm main body 30. The arm 3 is configured such that the tip end portion thereof can move relative to the base end portion thereof in a three-dimensional space. In the present embodiment, the plurality of arms 3 included in the patient-side system 1 are the same in configuration as one another or similar in configuration to one another. However, at least one of the plurality of arms 3 may be different in configuration from the other arms 3. A holder (tool holding portion) 36 capable of holding the long shaft-shaped surgical instrument is provided at the tip end portion of the arm 3. In the present embodiment, the holder 36 is provided at the tip end portion of the translational arm 35.

When the arm 3 is the instrument arm 3B, the instrument 42 is detachably held by the holder 36. The shaft 43 of the instrument 42 held by the holder 36 extends along the long axis direction D. Further, when the arm 3 is the camera arm 3A, the endoscope assembly 41 is detachably held by the holder 36. It should be noted that the holder 36 provided at the camera arm 3A may be different in shape or structure from the holder 36 provided at the instrument arm 3B. Or, since it is rare to replace the endoscope assembly 41 during surgery, the endoscope assembly 41 may be fixed to the camera arm 3A.

The arm 3 is configured to be attachable to and detachable from the platform 5. The arm 3 has water resistance, heat resistance, and chemical resistance for a cleaning treatment and a sterilization treatment. As the sterilization treatment of the arm 3, there are various methods. For example, high pressure steam sterilization, EOG sterilization, chemical sterilization using disinfectant, or the like may be selectively used.

The arm main body 30 includes: a base 80 detachably attached to the platform 5; and first to sixth links 81 to 86 sequentially coupled to one another from the base 80 to the tip end portion. More specifically, the base end portion of the first link 81 is coupled to the tip end portion of the base 80 through a twisting joint J31. The base end portion of the second link 82 is coupled to the tip end portion of the first link 81 through a twisting joint J32. The base end portion of the third link 83 is coupled to the tip end portion of the second link 82 through a bending joint J33. The base end portion of the fourth link 84 is coupled to the tip end portion of the third link 83 through a twisting joint J34. The base end portion of the fifth link 85 is coupled to the tip end portion of the fourth link 84 through a bending joint J35. The base end portion of the sixth link 86 is coupled to the tip end portion of the fifth link 85 through a twisting joint J36. The base end portion of the translational arm 35 is coupled to the tip end portion of the sixth link 86 through a bending joint J37. With this, the arm 3 is configured as a seven-axis articulated arm including a redundant axis (in the present embodiment, the twisting joint J32). Therefore, the arm 3 can change its posture without changing the position of the tip end portion of the arm 3.

An outer shell of the arm main body 30 is mainly formed by a material, such as stainless steel, having heat resistance and chemical resistance. Further, a seal (not shown) for obtaining water resistance is provided at a coupling portion where the links are coupled to each other. The seal has heat resistance for the high pressure steam sterilization and chemical resistance for the disinfectant. At the coupling portion where the links are coupled to each other, the end portion of one of the links is inserted into the end portion of the other of the links, and the seal is arranged so as to fill a gap between the end portions of the links. Therefore, the seal is not visible from outside. With this, water, a chemical liquid, and steam are prevented from entering through a gap between the seal and the link.

The translational arm 35 is a mechanism configured to translate the holder 36, attached to the tip end portion of the translational arm 35, in the long axis direction D to translate the instrument 42, attached to the holder 36, in a direction in which the shaft 43 extends.

The translational arm 35 includes: a base end-side link 61 coupled to the tip end portion of the sixth link 86 of the arm main body 30 through the bending joint J37; a tip end-side link 62; a connecting shaft 63 coupling the base end-side link 61 and the tip end-side link 62; and an interlock mechanism (not shown). A rotating shaft 68 is provided at the tip end portion of the translational arm 35, i.e., the tip end portion of the tip end-side link 62. A driving source of the translational arm 35 is provided at the tip end portion of the arm main body 30, i.e., the sixth link 86. The connecting shaft 63 is arranged parallel to the bending joint J37, and the tip end-side link 62 is configured to be rotatable relative to the base end-side link 61 about the connecting shaft 63. A known link mechanism is adoptable as the interlock mechanism. For example, a configuration including a pulley and a timing belt may be used, or a mechanism including a gear train may be used.

A first translational arm driving shaft and a second translational arm driving shaft (both not shown) arranged coaxially with the bending joint J37 are provided at the base end portion of the base end-side link 61 (a coupling portion coupled to the sixth link 86). The second translational arm driving shaft is coupled to the interlock mechanism, and the second translational arm driving shaft moves relative to the first translational arm driving shaft. With this, the translational arm 35 performs a translational operation while a ratio among a rotation angle of the base end-side link 61 around the bending joint J37, a rotation angle of the tip end-side link 62 around the connecting shaft 63, and a rotation angle of the holder 36 around the rotating shaft 68 is being maintained at a predetermined ratio (for example, 1:2:1). The first translational arm driving shaft and the second translational arm driving shaft rotate in sync with each other, and with this, the entire translational arm 35 rotates relative to the arm main body 30 about the bending joint J37.

Figure 3:
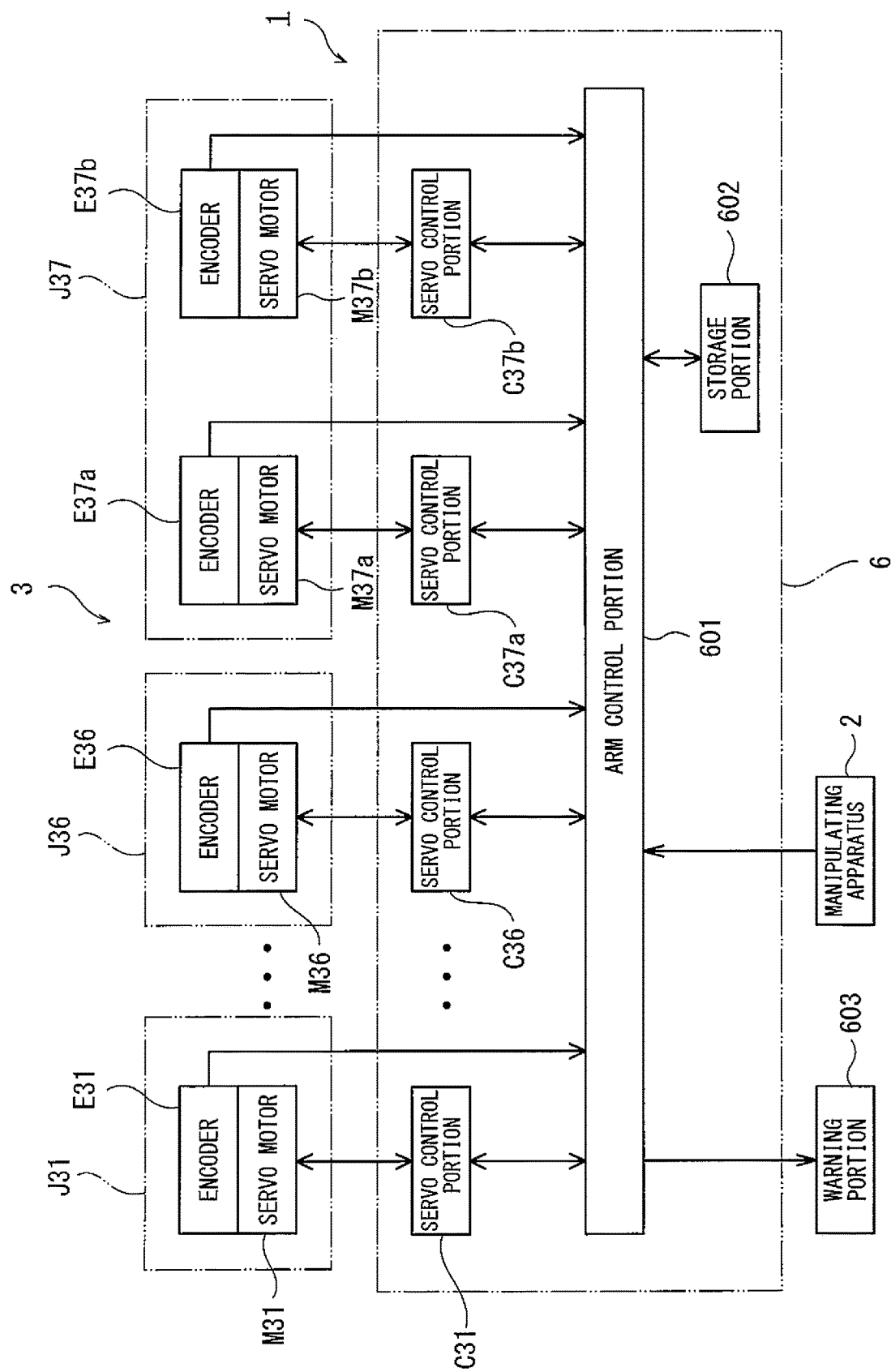
FIG. 3 is a block diagram showing a schematic configuration of control systems of the manipulator arm of the surgical system shown in FIG. 1.

FIG. 3 is a block diagram showing a schematic configuration of control systems of the manipulator arm of the surgical system shown in FIG. 1. In correspondence with the joints J31 to J36, the arm main body 30 configured as above is provided with: servo motors M31 to M36 for driving; encoders E31 to E36 configured to detect rotation angles of the servo motors M31 to M36; and reducers (not shown) configured to decelerate outputs of the servo motors M31 to M36 to increase torques of the servo motors M31 to M36. In FIG. 3, the control system of the twisting joint J31 and the control system of the twisting joint J36 are shown, and the control systems of the joints J33 to J35 are omitted. Further, in correspondence with the joint J37 by which the translational arm 35 performs the translational operation or a rotational operation, the arm main body 30 is provided with:

a servo motor M37a configured to drive the first translational arm driving shaft; a servo motor M37b configured to drive the second translational arm driving shaft; an encoder E37a configured to detect a rotation angle of the servo motor M37a; an encoder E37b configured to detect a rotation angle of the servo motor M37b; a reducer (not shown) configured to decelerate an output of the servo motor M37a to increase a torque of the servo motor M37a; and a reducer (not shown) configured to decelerate an output of the servo motor M37b to increase a torque of the servo motor M37b.

It should be noted that the encoder (E31 to E36, E37a, E37b) is provided as one example of a rotational position detecting device configured to detect a rotational position (rotation angle) of the corresponding servo motor (M31 to M36, M37a, M37b). Instead of the encoder (E31 to E36, E37a, E37b), the other rotational position detecting device, such as a resolver, may be used. Further, the above components of the control systems of the arm 3, and wires and control portions for those components are made of a high temperature resistant material, and therefore, has heat resistance for the sterilization treatment.

The controller 6 includes an arm control portion 601 configured to control the movements of the plurality of arms 3 based on the operating command. Servo control portions C31 to C36, C37a, and C37b are electrically connected to the arm control portion 601, and the servo motors M31 to M36, M37a, and M37b are electrically connected to the arm control portion 601 through an amplifying circuit (not shown) and the like.

In the above configuration, a position posture command of the tip end portion of the arm 3 is input to the arm control portion 601 based on the operating command input to the manipulating apparatus 2. The arm control portion 601 generates and outputs a position command value based on the position posture command and the rotation angles detected by the encoders E31 to E36, E37a, and E37b. The servo control portion (C31 to C36, C37a, C37b) which has acquired the position command value generates and outputs a drive command value (torque command value) based on the position command value and the rotation angle detected by the corresponding encoder (E31 to E36, E37a, E37b). The amplifying circuit which has acquired the drive command value supplies a drive current corresponding to the drive command value to the servo motors M31 to M36, M37a, and M37b. Thus, the servo motors M31 to M36, M37a, and M37b are controlled such that the position and posture of the tip end portion of the arm 3 become the position and posture corresponding to the position posture command.

The controller 6 includes a storage portion 602 from which the arm control portion 601 can read out data. The storage portion 602 prestores surgery information input through the manipulating apparatus 2. The surgery information contains a combination of the plurality of arms 3 used in surgery.

Further, the storage portion 602 stores information, such as lengths of the surgical instruments (the endoscope assembly 41 and the instruments 42) in the long axis direction D, the surgical instruments being held by the respective tip end portions of the arms 3. With this, based on the position posture command of the tip end portion of the arm 3, the arm control portion 601 can recognize the position of the tip end portion of the surgical instrument held by the tip end portion of the arm 3.

During the medical treatment using the surgical system 100, the arm control portion 601 performs interference determination processing of determining based on the operating command from the manipulating apparatus 2 whether or not the plurality of arms 3 interfere with one another. When it is determined in the interference determination processing that the interference occurs, the arm control portion 601 executes interference preventing processing.

The storage portion 602 stores interference determination processing data for executing the interference determination processing. Here, a first point group model (first lattice model) is set so as to correspond to a first arm (for example, the camera arm 3A; hereinafter may be referred to as a first arm 3A) and is created by arranging a plurality of points (lattice points) on a surface of a predetermined stereoscopic shape defining a three-dimensional movement range of the tip end portion of a first surgical instrument (for example, the endoscope assembly 41) held by the first arm 3A. Similarly, a second point group model (second lattice model) is set so as to correspond to a second arm (for example, the instrument arm 3B; hereinafter may be referred to as a second arm 3B) adjacent to the first arm 3A and is created by arranging a plurality of points (lattice points) on a surface of a stereoscopic shape defining a three-dimensional movement range of the tip end portion of a second surgical instrument (for example, the instrument 42) held by the second arm 3B. The interference determination processing data is configured as data of such a combination of one point in the first lattice model and one point in the second lattice model that a first posture formed by the first arm 3A and the first surgical instrument 41 when the tip end portion of the first surgical instrument 41 is located at a three-dimensional position of each point in the first lattice model and a second posture formed by the second arm 3B and the second surgical instrument 42 when the tip end portion of the second surgical instrument 42 is located at a three-dimensional position of each point in the second lattice model interfere with each other.

Figure 4:
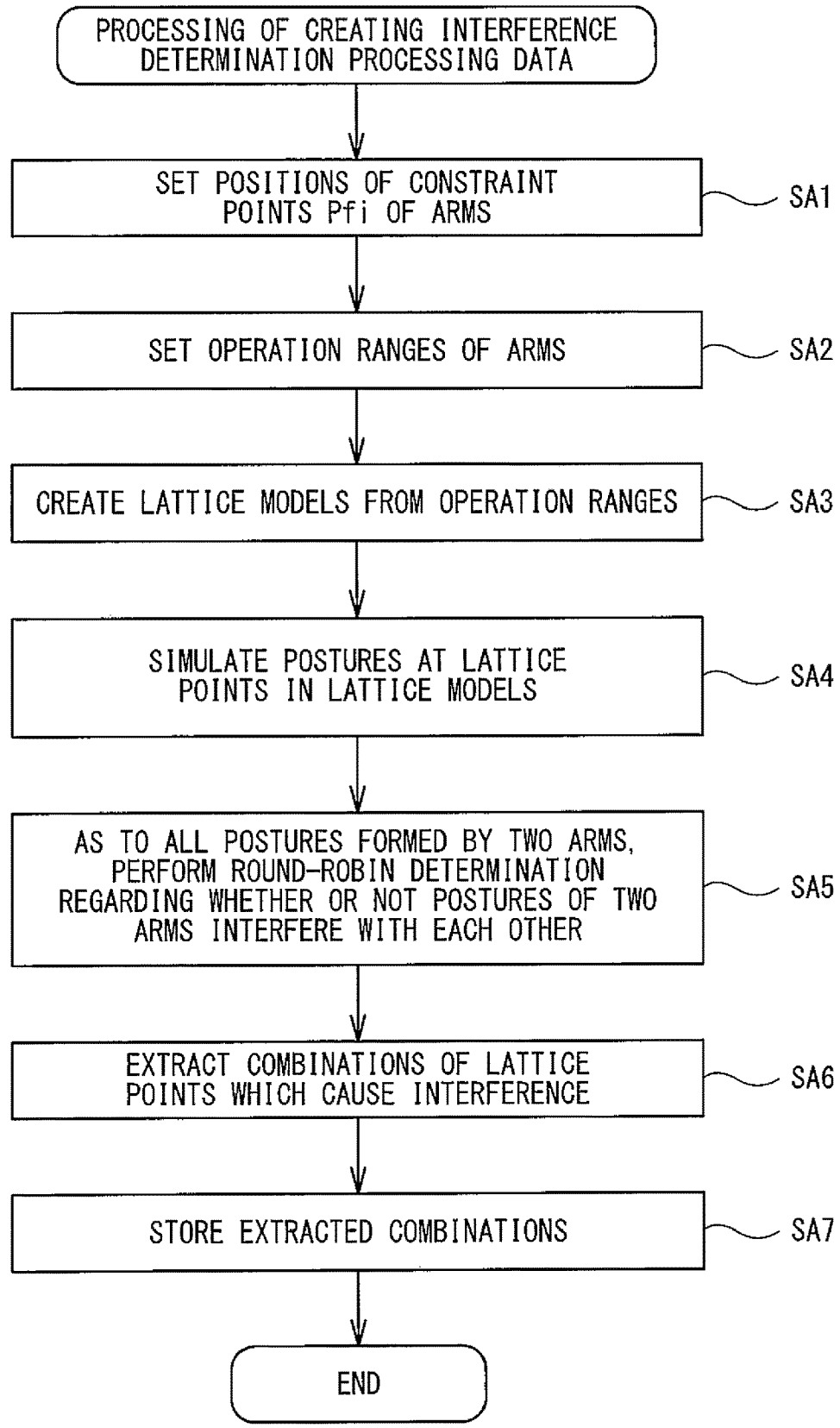
FIG. 4 is a flow chart for explaining a flow of processing of creating interference determination processing data for interference determination processing in the present embodiment.
Figure 5:
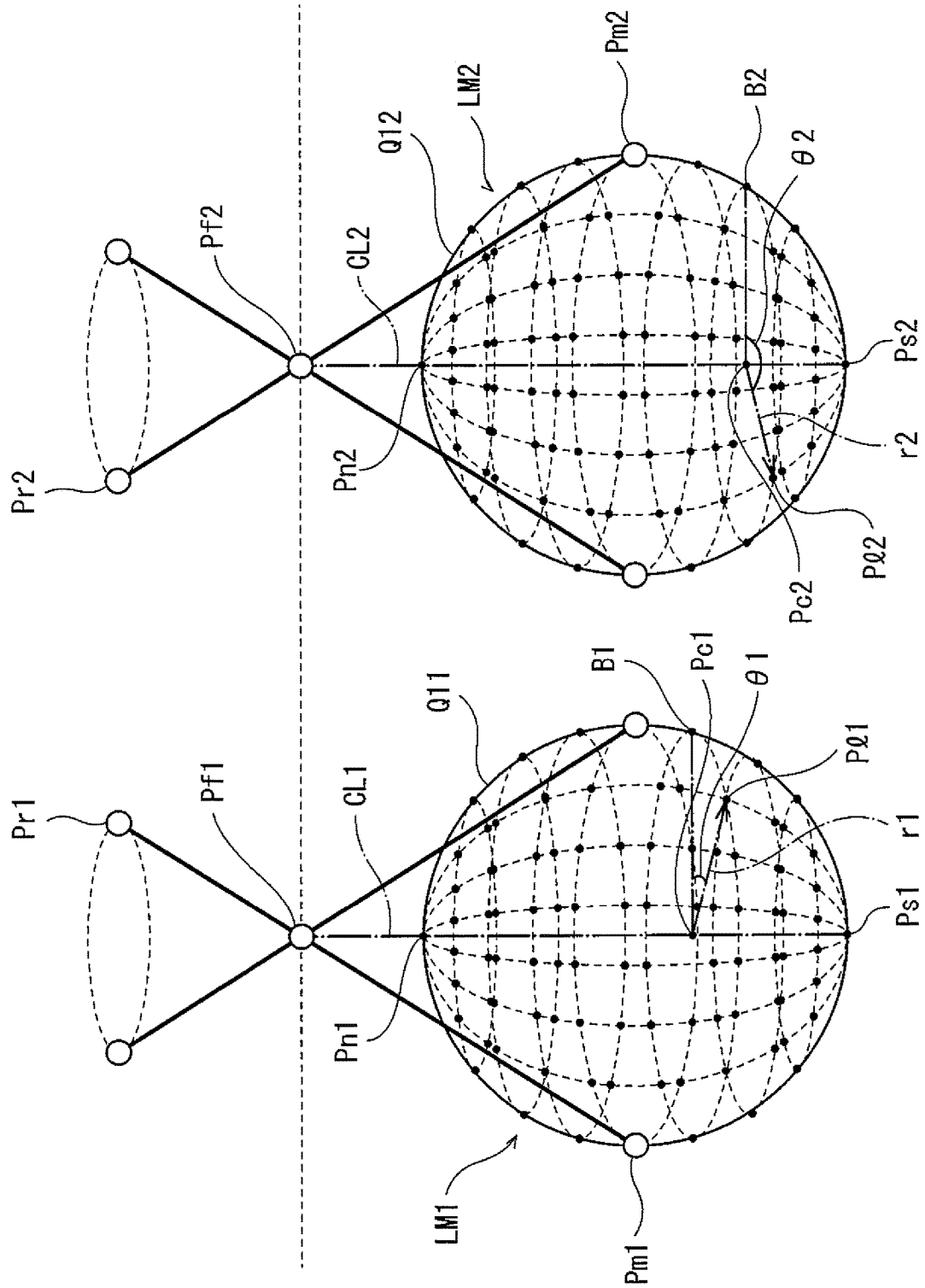
FIG. 5 is a conceptual diagram showing examples of first and second lattice models created in FIG. 4.

Hereinafter, processing of creating the interference determination processing data will be explained. FIG. 4 is a flow chart for explaining a flow of the processing of creating the interference determination processing data in the present embodiment. FIG. 5 is a conceptual diagram showing examples of the first and second lattice models created in FIG. 4. The interference determination processing data explained below may be created by the controller 6 based on a data creating program stored in the storage portion 602 and be stored in the storage portion 602. Or, the interference determination processing data explained below may be created by an external computer and be stored in the storage portion 602.

In the processing of creating the interference determination processing data, first, a predetermined position (i.e., a predetermined position on the surgical instrument) between a tip end portion Pri (i denotes an identification number of each arm 3) of each arm 3 and a tip end portion Pmi of the surgical instrument held by the arm 3 is set as a constraint point Pfi (Step SA1). The three-dimensional position of the constraint point Pfi is set so as to correspond to the opening position of the patient P when the surgical instrument is inserted into the body of the patient P through the sleeve 110 placed on the patient P.

Next, the position of the surgical instrument (for example, the position of the tip end portion of the surgical instrument) is set as a reference point. Then, the three-dimensional movement range of the reference point of the surgical instrument when the arm 3 is moved three-dimensionally with the three-dimensional position of the constraint point Pfi fixed is set as a predetermined stereoscopic shape (Step SA2). The stereoscopic shape defines approximate boundary positions of the tip end portion of the surgical instrument when the surgical instrument is inserted into the body of the patient P through the opening position located at the constraint point Pfi.

In the present embodiment, the predetermined stereoscopic shape is a sphere (first virtual sphere Q1i). Further, each of predetermined point group models LMi is created by arranging a plurality of points Pli on a surface of the stereoscopic shape set as the movement range (Step SA3). For example, the plurality of points Pli arranged on the surface of the first virtual sphere Q1i are set as intersection points (lattice points) between a plurality of longitudinal lines and a plurality of latitudinal lines. Each of the plurality of longitudinal lines extends on the surface of the first virtual sphere Q1i and connects pole points Pni and Psi. The plurality of latitudinal lines are defined by circumferences of a section perpendicular to a straight line CLi and sections parallel to the section perpendicular to the straight line CLi. The straight line CLi couples the center of the first virtual sphere Q1i and the constraint point Pfi. The pole points Pni and Psi are two points at each of which the straight line CLi intersects with the surface of the first virtual sphere Q1i. In this case, each of the point group models LMi is set as a lattice model LMi on which the plurality of lattice points Pli are arranged.

Three-dimensional coordinates of the points Pli in the plurality of point group models LMi are stored in the storage portion 602. In the present embodiment in which the lattice model having the spherical shape is set as the movement range, the position coordinates of each lattice point Pli in the lattice model LMi are determined, for example, based on: the position coordinates of a center point Pci of a section of the sphere, the section being perpendicular to the straight line CLi coupling the corresponding constraint point Pfi and the center of the sphere; a radius ri of the section; and an angle θi from a predetermined reference position Bi on the lattice model LMi. With this, the position coordinates of the lattice points Pli can be easily determined, and the positions of the combinations which cause below-described interference can be easily recognized.

The lattice points Pli and the lattice models LMi corresponding to the respective arms 3 are individually set in accordance with contents of the surgical instruments held by the arms 3, contents of the surgery, the treated part, the size of the patient P, and/or the like. Therefore, the adjacent lattice models LMi may at least partially overlap each other or may not overlap each other. Further, the size of the lattice model LMi (the radius of the first virtual sphere Q1i) and the distance between the corresponding constraint point Pfi and the lattice model LMi (the center of the first virtual sphere Q1i) may vary depending on, for example, the type or size of the surgical instrument held by the arm 3.

Next, the postures formed by the arm 3 and the surgical instrument when the reference point (tip end portion) of the surgical instrument is located at the respective three-dimensional positions of the lattice points Pli in the lattice model LMi set so as to correspond to the arm 3 are acquired by simulation (Step SA4). The acquired postures may contain: the three-dimensional positions of the joints J31 to J37 of the arm 3; the three-dimensional position of the tip end portion (the holder 36) of the arm 3; the three-dimensional position of the tip end portion of the surgical instrument held by the holder 36; the sizes (for example, the diameters) of sections, perpendicular to a direction in which the arm extends, of respective portions of the arm 3; and the like. For example, the simulation for acquiring the postures is performed by using computer graphics (CG) models having the same shapes as the arm 3 and the surgical instrument. Instead of this, the postures may be acquired by simulation performed only by numerical calculation.

For example, simulated is the first posture formed by the first arm 3A and the endoscope assembly 41 when the tip end portion of the endoscope assembly 41 is located at the three-dimensional position of each lattice point Pl1 in the first lattice model LM1 set so as to correspond to the first arm 3A, the endoscope assembly 41 being held by the first arm 3A. In addition, simulated is the second posture formed by the second arm 3B and the instrument 42 when the tip end portion of the instrument 42 is located at the three-dimensional position of each lattice point Pl2 in the second lattice model LM2 set so as to correspond to the second arm 3B, the second arm 3B being located adjacent to the first arm 3A, the instrument 42 being held by the second arm 3B.

Next, regarding all the combinations of the lattice points (Pl1, Pl2) in the lattice models LM1 and LM2 set for the adjacent arms 3A and 3B, whether or not the first posture and the second posture interfere with each other is determined (Step SA5). In addition, whether or not the posture formed by the arm 3 and the surgical instrument when the tip end portion of the surgical instrument is located at each lattice point Pli interfere with itself is also determined. For example, the CG models are arranged at set positions, and whether or not the CG models interfere with one another is determined. Such determination is performed in a round robin for all the postures formed by the two arms 3 which may interfere with each other among the plurality of arms 3. To be specific, such determination is performed for all the combinations of the lattice points Pli at which the arms 3 may be located.

For example, determined is whether or not the first posture formed by the first arm 3A and the endoscope assembly 41 at one lattice point Pl1 in the first lattice model LM1 interferes with each of the second postures formed by the second arm 3B and the instrument 42 at all the lattice points Pl2 in the second lattice model LM2. Similarly, determined is whether or not the first posture at another lattice point Pl1 in the first lattice model LM1 interferes with each of the second postures at all the lattice points Pl2 in the second lattice model LM2. By performing such determination for all the lattice points Pl1 in the first lattice model LM1, the round-robin determination is performed.

As a result of the determination, stored in the storage portion 602 is the data of such combination of the lattice point in the first lattice model LM1 and the lattice point in the second lattice model LM2 that the first arm 3A and the first surgical instrument (endoscope assembly 41) in the first posture and the second arm 3B and the second surgical instrument (instrument 42) in the second posture interfere with each other. In the present embodiment, such combination of the lattice point Pl1 in the first lattice model LM1 and the lattice point Pl2 in the second lattice model LM2 that the first posture and the second posture interfere with each other is extracted (Step SA6), and the data of the combination (Pl1, Pl2) which causes the interference is stored in the storage portion 602 as the interference determination processing data (Step SA7).

The interference determination processing data stored in the storage portion 602 as above may be stored as, for example, a list containing the combinations of the lattice points (Pl1, Pl2) which cause the interference or a data map in which data indicating whether or not the interference occurs regarding all the combinations of the lattice points Pl1 in the first lattice model LM1 and the lattice points Pl2 in the second lattice model LM2 is associated with the combinations of the lattice points.

After the first postures at the respective lattice points Pl1 and the second postures at the respective lattice point Pl2 are acquired by simulation, whether or not the first posture and the second posture interfere with each other may be determined for all the combinations of the lattice points Pl1 and the lattice points Pl2. Or, whether or not the first posture and the second posture interfere with each other may be determined each time the first posture at one lattice point Pl1 and the second posture at one lattice point Pl2 are acquired.

Further, when the combination which causes the interference is extracted, whether or not the interference occurs by changing at least one of the first posture and the second posture without changing the position of the tip end portion of the arm 3 may be redetermined. When the interference does not occur as a result of the redetermination, the changed first and second postures are stored in the storage portion 602 as the postures at the corresponding lattice points Pli and are not stored as the combination which causes the interference. With this, the number of combinations which cause the interference can be reduced as much as possible.

Figure 6:
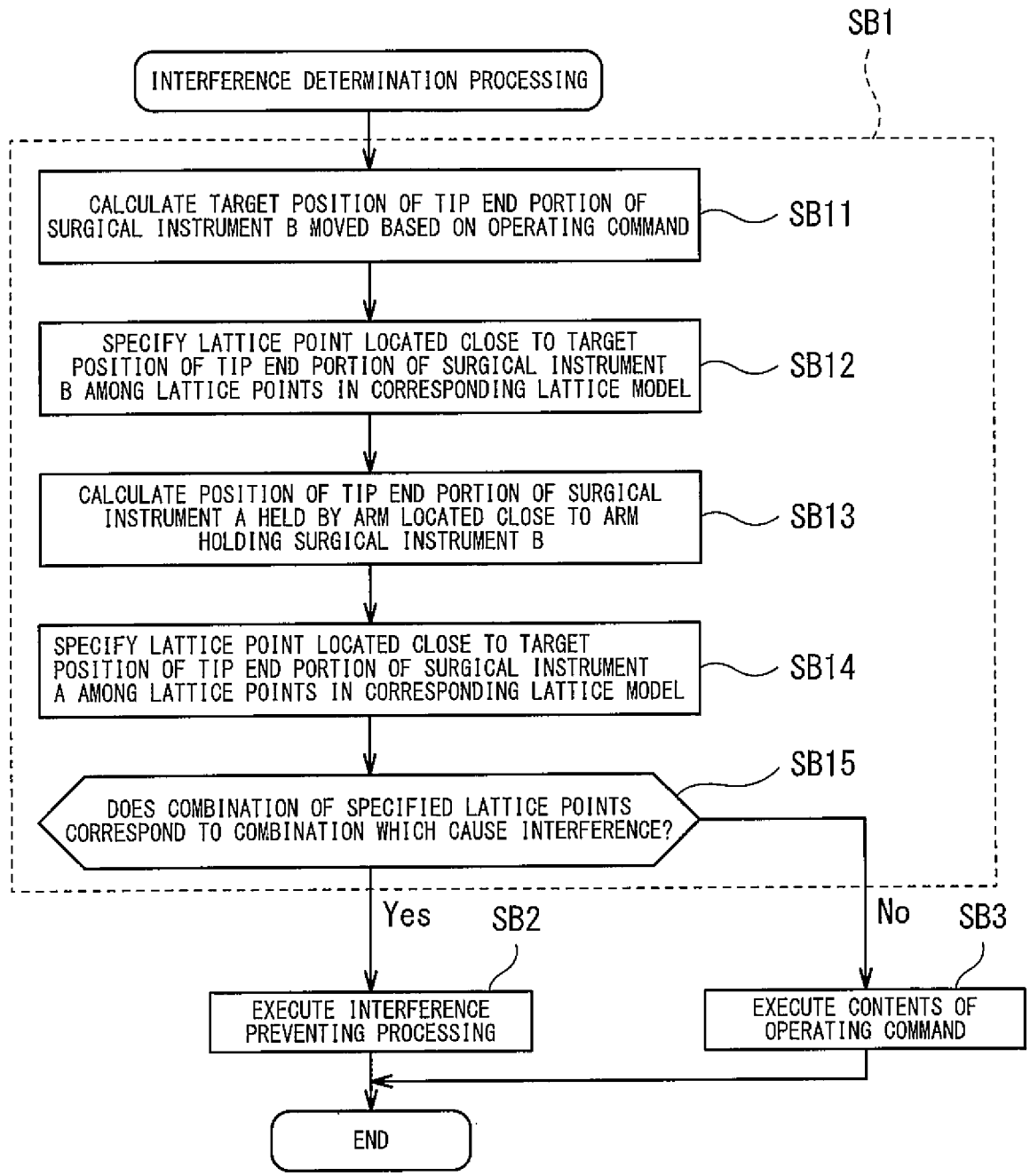
FIG. 6 is a flow chart for explaining a flow of the interference determination processing in the present embodiment.

The arm control portion 601 executes the interference determination processing by using the interference determination processing data. FIG. 6 is a flow chart for explaining the flow of the interference determination processing in the present embodiment.

The arm control portion 601 determines whether or not the operating command transferred from the manipulating apparatus 2 to the arm control portion 601 corresponds to the combination which causes the interference (Step SB1). For example, as in the above example, when the operating command contains a command of moving the second arm 3B holding the instrument 42 (shown as the surgical instrument B in FIG. 6), the arm control portion 601 calculates a movement target position of the tip end portion of the instrument 42, held by the second arm 3B, from a movement target position of the tip end portion of the second arm 3B (Step SB11) and specifies the lattice point Pl2 located close to the three-dimensional position of the tip end portion of the instrument 42 among the lattice points Pl2 in the lattice model LM2 (Step SB12). For example, the arm control portion 601 specifies the lattice point Pl2 located closest to the movement target position of the tip end portion of the instrument 42. Or, for example, the arm control portion 601 specifies the lattice point Pl2 located closest to the movement target position of the tip end portion of the instrument 42 among the lattice points Pl2 located on a movement path extending from a current position of the tip end portion of the instrument 42 to the movement target position of the tip end portion of the instrument 42.

Further, the arm control portion 601 calculates the three-dimensional position of the tip end portion of the endoscope assembly 41 (shown as the surgical instrument A in FIG. 6) held by the first arm 3A located close to the moving second arm 3B (Step SB13) and specifies the lattice point Pl1 located close to the three-dimensional position of the tip end portion of the endoscope assembly 41 among the lattice points Pl1 of the lattice model LM1 (Step SB14). Then, the arm control portion 601 determines by using the storage portion 602 whether or not the combination of the specified lattice point Pl1 and the specified lattice point Pl2 corresponds to the combination which causes the interference (Step SB15).

It should be noted that in a case where the first arm 3A does not move, the arm control portion 601 may specify the lattice point Pl1 located close to the three-dimensional position of the tip end portion of the endoscope assembly 41 when the previous operating command of moving the first arm 3A is received, and may store the specified lattice point PL1 in the storage portion 602 as the current position in the first lattice model LM1. In this case, Steps SB13 and SB14 are executed beforehand. Further, at the time of the determination of the interference, after Step SB12, instead of Steps SB13 and SB14, the arm control portion 601 reads out the lattice point PL1 indicating the current position in the first lattice model LM1 from the storage portion 602 and performs the determination in Step SB15.

Further, when the arms 3 located close to each other move at the same time, the arm control portion 601 calculates the movement target positions of the tip end portions of the surgical instruments held by the arms 3 from the movement target positions of the arms 3 and specifies the lattice points Pli in the corresponding lattice models LMi.

When it is determined that the operating command corresponds to the combination which causes the interference (Yes in Step SB15), the arm control portion 601 executes the predetermined interference preventing processing (Step SB2). In contrast, when it is determined that the operating command does not correspond to the combination which causes the interference (No in Step SB15), the arm control portion 601 executes contents of the operating command (Step SB3).

The foregoing has explained an example in which it is determined whether or not the instrument arm 3B exemplified as the second arm and holding the instrument 42 interferes with the camera arm 3A exemplified as the first arm and holding the endoscope assembly 41 when the instrument arm 3B is moved. However, the above embodiment is applicable to the determination of the interference when the camera arm 3A is moved, the determination of the interference between the arms 3 holding the respective instruments 42, and the like. To be specific, the above embodiment is applicable to the determination of the interference regardless of the type of the surgical instrument held by the moving arm 3 and whether the surgical instruments of the two arms are the same as each other or different from each other.

According to the above aspect, the positions of the surgical instruments are set as the reference points. Further, the positions of the plurality of manipulator arms and the surgical instruments are simulated by using the lattice models LMi, on each of which the plurality of lattice points Pli are arranged, as the movement ranges of the reference points. Especially, according to the present embodiment, the position corresponding to the opening position at which the surgical instrument is inserted into the body of the patient P is set as the constraint point Pfi. Further, the three-dimensional movement range of the tip end portion of the surgical instrument when the arm 3 is three-dimensionally moved with the three-dimensional position of the constraint point Pfi fixed is set as the predetermined lattice model LMi created by arranging the plurality of lattice points Pli on the surface of the predetermined stereoscopic shape. The posture formed by the arm 3 and the surgical instrument when the tip end portion of the surgical instrument is located at each lattice point Pli constituting the lattice model LMi set for the arm 3 is simulated. It is determined whether or not the first posture formed by the first arm and the first surgical instrument and the second posture formed by the adjacent second arm and the second surgical instrument interfere with each other. Then, the combinations of the lattice points (Pl1, Pl2) which cause the interference are stored in the storage portion 602 of the surgical system 100 before the medical treatment.

When it is determined during the medical treatment that the combination of the postures of the plurality of arms 3 based on the operating command input by the operator O corresponds to the combination of the lattice points (Pl1, Pl2) which cause the interference, the interference preventing processing is executed to prevent the interference from actually occurring. As above, the combinations which cause the interference of the first and second postures are extracted in advance by the round-robin determination for the plurality of lattice points Pli defining the movement ranges set for the respective arms 3. With this, processing of avoiding the interference can be performed without performing complex calculations while moving the arms 3 during the medical treatment. Therefore, the plurality of arms 3 can be prevented from interfering with one another while suppressing influences on the medical treatment, such as restrictions on the speed and position of the medical treatment.

The surgical system 100 includes a predetermined informing portion 603. The informing portion 603 is connected to the arm control portion 601. When the informing portion 603 receives a warning output signal from the arm control portion 601, the informing portion 603 outputs a predetermined warning. In this configuration, the arm control portion 601 may be configured to output a warning through the informing portion 603 as the interference preventing processing. The informing portion 603 may be a tool configured to visually or audibly inform the operator O of the warning, such as a speaker, a siren, and a warning light, or may be configured to display the warning on a display, such as the monitor 53 provided at the manipulating apparatus 2. Further, the informing portion 603 may be configured to inform the operator O of the warning by vibrating the operation manipulator arm 51 to which the operator O inputs the operating command or by applying force (resistance force) to the operation manipulator arm 51 in a direction opposite to a direction in which the operator O inputs. As above, by outputting the warning from the informing portion 603, the input of the operating command which causes the interference can be quickly informed to the operator O.

The interference preventing processing may be processing in which the arm control portion 601 performs a control operation of preventing at least one of the first arm 3A and the second arm 3B from moving to the position of the combination (Pl1, Pl2) which causes the interference. With this, even when the operating command which causes the interference is input, the interference can be prevented from actually occurring.

It should be noted that after the informing portion 603 outputs the warning and if the operator O again inputs the operating command which causes the interference, the arm control portion 601 may stop the movements of the arms 3 as the interference preventing processing.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

For example, the stereoscopic shape defining the movement range of the tip end portion of the surgical instrument may be a shape other than the sphere. For example, the stereoscopic shape may be a rectangular solid shape, a columnar shape, a prism shape, or a regular polyhedron shape (a regular tetrahedron shape, a cube shape, a regular octahedron shape, a regular dodecahedron shape, or a regular icosahedron shape).

The above embodiment has explained an example in which in the interference determination processing, one lattice point Pl2 located close to the movement target position of the tip end portion of the surgical instrument held by the second arm 3B is specified (Step SB12). However, when the movement target position of the surgical instrument does not coincide with the lattice point Pl2 (or when the movement target position of the surgical instrument cannot be specified to any of the lattice points Pl2), the arm control portion 601 may (i) specify a plurality of lattice points Pl2 located around the movement target position, (ii) determine whether or not each of the combinations of the specified plurality of lattice points Pl2 and one or a plurality of lattice points Pl1 located close to the tip end portion of the surgical instrument held by the first arm 3A corresponds to the combination which causes the interference, and (iii) perform the interference preventing processing based on the result of the determination.

In this case, for example, there may be plural types of interference preventing processing, and when the number of combinations which cause the interference in the combinations of the lattice points (Pl1, Pl2) as determination targets is large, heavy interference preventing processing may be performed. For example, light interference preventing processing may be processing of outputting the warning through the informing portion 603, and the heavy interference preventing processing may be processing of stopping the movements of the arms 3.

In the case of specifying the plurality of lattice points Pl2 located around the movement target position, the movement path of the second arm 3B may be considered. For example, among the plurality of lattice points Pl2 located around the movement target position, the lattice points Pl2 located at an opposite side of the current position of the tip end portion of the surgical instrument may excluded from the determination targets. Or, for example, among the plurality of lattice points Pl2 located around the movement target position, the lattice points Pl2 located at an opposite side of the current position of the tip end portion of the surgical instrument may be regarded as the determination targets but be made lower in influence than the other lattice points Pl2. One example may be such that: when only the lattice points Pl2 located at an opposite side of the current position are included in the combinations which cause the interference, the arm control portion 601 performs the light interference preventing processing; and when the other lattice points Pl2 (i.e., the lattice points located at the current position side) are included in the combinations which cause the interference, the arm control portion 601 performs the heavy interference preventing processing.

Figure 7:
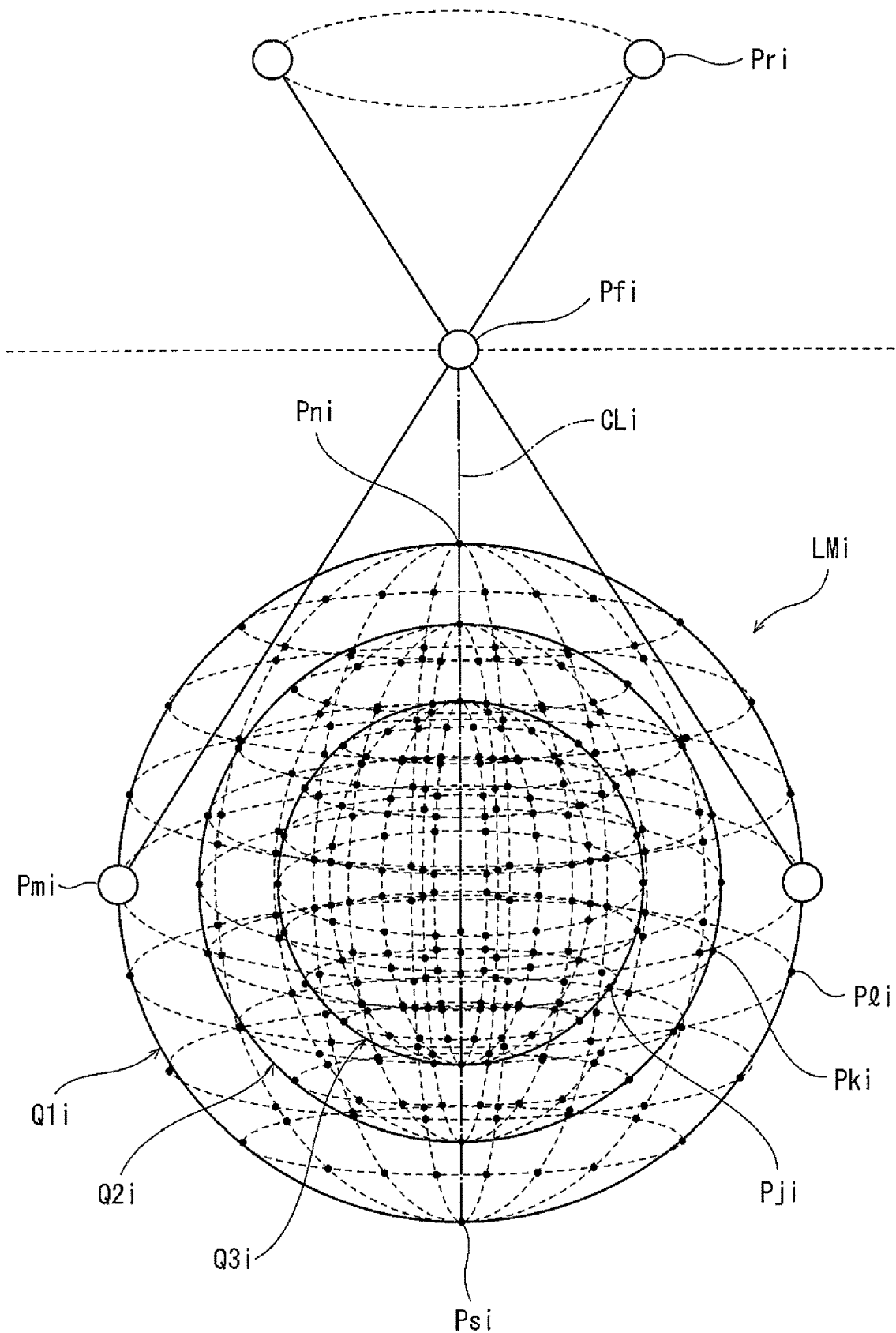
FIG. 7 is a conceptual diagram showing an example of a lattice model according to Modified Example of the present embodiment.

Further, the lattice model LMi may be created such that the lattice points are also included inside the stereoscopic shape (for example, the first virtual sphere Q1) defining the movement range. For example, the center position of the lattice model LMi may be located at the same position as the center position of the stereoscopic shape defining the movement range, and the lattice model LMi may include lattice points Pki arranged on the surface of a shape similar to but smaller than the stereoscopic shape defining the movement range. FIG. 7 is a conceptual diagram showing an example of the lattice model according to Modified Example of the present embodiment.

As shown in FIG. 7, the lattice model LMi according to the present modified example includes the first virtual sphere Q1$i$, a second virtual sphere Q2$i$, and a third virtual sphere Q3$i$. The first virtual sphere Q1$i$ defines the movement range of the surgical instrument. The second virtual sphere Q2$i$ has a center position located at the same position as the center position of the first virtual sphere Q1$i$, and has a radius shorter than the radius of the first virtual sphere Q1$i$. The third virtual sphere Q3$i$ has a center position located at the same position as the center position of the first virtual sphere Q1$i$, and has a radius shorter than the radius of the second virtual sphere Q2$i$. It should be noted that the number of virtual spheres may be two or four or more. As with the example shown in FIG. 4, a plurality of lattice points Pli are arranged on the surface of the first virtual sphere Q1$i$. A plurality of lattice points Pki are arranged on the surface of the second virtual sphere Q2$i$. A plurality of lattice points Pji are arranged on the surface of the third virtual sphere Q3$i$.

By using the lattice models LMi created as above, the first postures and the second postures when the tip end portions of the surgical instruments are located at the lattice points Pli, Pki, and Pji in the lattice models LM1 and LM2 corresponding to the two adjacent arms 3 can be simulated. Therefore, the combinations which cause the interference between the first posture and the second posture can be determined in a round robin for the plurality of lattice points Pli, Pki, and Pji defining the boundaries and insides of the movement ranges set for the respective arms 3. For example, it is determined whether or not the first posture at one lattice point Pl1 in the first lattice model LM1 and the second posture at one lattice point Pk2 in the second lattice model LM2 interfere with each other. Therefore, by using the lattice model LMi created as above, the posture formed by the arm 3 and the surgical instrument when the tip end portion of the surgical instrument is located inside the movement range can also be considered. Thus, the determination of the interference can be performed more accurately. The lattice model LMi created as above is applicable to not only when the stereoscopic shape defining the movement range is a sphere but also when the stereoscopic shape defining the movement range is any of the other stereoscopic shapes described above. Further, the aspect in which the lattice points are arranged inside the stereoscopic shape defining the movement range is not limited to the above and can be suitably set.

The point group model that is the model of the movement range of the reference point set as the position of the surgical instrument is not especially limited as long as the plurality of points constituting the point group model are arranged in the movement range of the reference point. To be specific, the point group model may be not only the lattice model provided with the intersection points (lattice points) of the plurality of lines as in the above embodiment but also, for example, a model including a plurality of points arranged randomly in a predetermined three-dimensional region.

INDUSTRIAL APPLICABILITY

Each of the surgical system control method and the surgical system according to the present invention is useful to prevent a plurality of manipulator arms from interfering with one another without influencing a medical treatment.

REFERENCE SIGNS LIST 2 manipulating apparatus
3 arm (manipulator arm)
36 holder (tool holding portion)
41 endoscope assembly (surgical instrument)
42 instrument (surgical instrument)
100 surgical system
601 arm control portion (control portion)
602 storage portion
603 informing portion

The invention claimed is:

1. A method of controlling a surgical system,
the surgical system comprising:
a plurality of manipulator arms each including a tool holding portion at a tip end portion of the manipulator arm, the tool holding portion being configured to hold a long shaft-shaped surgical instrument, the tip end portion of the manipulator arm being configured to three-dimensionally move relative to a base end portion of the manipulator arm;
a manipulating apparatus to which an operating command is input, the operating command being for moving the plurality of manipulator arms;
a control portion configured to control the movements of the plurality of manipulator arms based on the operating command; and
a storage portion from which the control portion reads out data,
the method comprising:
setting as a constraint point a predetermined position between the tip end portion of each manipulator arm and a tip end portion of the surgical instrument held by the manipulator arm;
setting a predetermined lattice model created by arranging a plurality of lattice points on a surface of a predetermined stereoscopic shape defining a three-dimensional movement range of the tip end portion of the surgical instrument when the manipulator arm is three-dimensionally moved with a three-dimensional position of the constraint point fixed;
simulating a first posture formed by a first manipulator arm and a first surgical instrument when a tip end portion of the first surgical instrument is located at the three-dimensional position of each lattice point in a first lattice model set so as to correspond to the first manipulator arm, the first surgical instrument being held by the first manipulator arm;
simulating a second posture formed by a second manipulator arm and a second surgical instrument when a tip end portion of the second surgical instrument is located at the three-dimensional position of each lattice point in a second lattice model set so as to correspond to the second manipulator arm, the second manipulator arm being located adjacent to the first manipulator arm, the second surgical instrument being held by the second manipulator arm;
extracting such a combination of the lattice point in the first lattice model and the lattice point in the second lattice model that the first posture and the second posture interfere with each other;
storing, in the storage portion, data of the combination which causes the interference;
determining whether or not the operating command transferred to the control portion corresponds to the combination which causes the interference; and
executing interference preventing processing by the control portion when it is determined that the operating command corresponds to the combination which causes the interference.

2. The method according to claim 1, wherein:
the stereoscopic shape is a sphere; and
position coordinates of each lattice point in the first and second lattice models are determined based on (i) position coordinates of a center point of a section of the sphere, the section being perpendicular to a straight line coupling the corresponding constraint point and a center of the sphere, (ii) a radius of the section, and (iii) an angle from a predetermined reference position on each lattice model.

3. The method according to claim 1 or 2, claim 1, wherein:
the surgical system includes a predetermined informing portion; and
the interference preventing processing includes an output of a warning from the informing portion.

4. The method according to claim 1, wherein as the interference preventing processing, the control portion prevents at least one of the first manipulator arm and the second manipulator arm from moving to a position of the combination which causes the interference.

5. The method according to claim 1, wherein:
each of the plurality of manipulator arms is configured as a seven-axis articulated arm including a redundant axis, the arm being configured to change a posture of the arm without changing a position of the tip end portion of the arm; and
when the combination which causes the interference is extracted, it is redetermined whether or not the interference occurs by changing at least one of the first posture and the second posture without changing the position of the tip end portion of each manipulator arm.

6. The method according to claim 1, wherein:
each of a center position of the first lattice model and a center position of the second lattice model is located at the same position as a center position of the corresponding stereoscopic shape; and
each of the first lattice model and the second lattice model includes lattice points arranged on a surface of a shape similar to but smaller than the corresponding stereoscopic shape.

7. A method of controlling a surgical system,
the surgical system comprising:
a plurality of manipulator arms each including a tool holding portion configured to hold a surgical instrument;
a control portion configured to control movements of the plurality of manipulator arms based on an operating command; and
a storage portion connected to the control portion,
the method comprising:
setting a first reference point as a position of a first surgical instrument held by a first manipulator arm;
setting a first point group model created by arranging a plurality of points in a movement range of the first reference point;
simulating a first posture formed by the first manipulator arm and the first surgical instrument when the first reference point is located at a position of each point in the first point group model;
setting a second reference point as a position of a second surgical instrument held by a second manipulator arm;
setting a second point group model created by arranging a plurality of points in a movement range of the second reference point;
simulating a second posture formed by the second manipulator arm and the second surgical instrument when the second reference point is located at a position of each point in the second point group model;
storing, in the storage portion, data of such a combination of the point in the first point group model and the point in the second point group model that the first manipulator arm and the first surgical instrument in the first posture and the second manipulator arm and the second surgical instrument in the second posture interfere with each other;
determining whether or not positions of the first and second reference points corresponding to the operating command transferred to the control portion correspond to the stored data of the combination; and
executing interference preventing processing by the control portion when it is determined that the positions correspond to the stored data.

8. A surgical system comprising:
a plurality of manipulator arms each including a tool holding portion at a tip end portion of the manipulator arm, the tool holding portion being configured to hold a long shaft-shaped surgical instrument, the tip end portion of the manipulator arm being configured to three-dimensionally move relative to a base end portion of the manipulator arm;
a manipulating apparatus to which an operating command is input, the operating command being for moving the plurality of manipulator arms;
a control portion configured to control the movements of the plurality of manipulator arms based on the operating command; and
a storage portion from which the control portion reads out data, wherein:
a first lattice model is set so as to correspond to a first manipulator arm and is created by arranging a plurality of lattice points on a surface of a predetermined stereoscopic shape defining a three-dimensional movement range of a tip end portion of a first surgical instrument held by the first manipulator arm;
a second lattice model is set so as to correspond to a second manipulator arm located adjacent to the first manipulator arm and is created by arranging a plurality of lattice points on a surface of a stereoscopic shape defining a three-dimensional movement range of a tip end portion of a second surgical instrument held by the second manipulator arm;
the storage portion stores data of such a combination of the lattice point in the first lattice model and the lattice point in the second lattice model that a first posture formed by the first manipulator arm and the first surgical instrument when the tip end portion of the first surgical instrument is located at a three-dimensional position of each lattice point in the first lattice model and a second posture formed by the second manipulator arm and the second surgical instrument when the tip end portion of the second surgical instrument is located at a three-dimensional position of each lattice point in the second lattice model interfere with each other;
the control portion determines whether or not the received operating command corresponds to the combination which causes the interference; and
when it is determined that the operating command corresponds to the combination which causes the interference, the control portion executes interference preventing processing.

* * * * *